(12) United States Patent
Di Maio

(10) Patent No.: US 11,918,617 B2
(45) Date of Patent: Mar. 5, 2024

(54) COMPOSITION FOR THE TREATMENT OF METABOLIC AND MECHANICAL NEUROPATHIES

(71) Applicant: NEILOS S.R.L., Piano di Sorrento (IT)

(72) Inventor: Umberto Di Maio, Piano di Sorrento (IT)

(73) Assignee: NEILOS S.R.L., Piano di Sorrento (IT)

( * ) Notice: Subject to any disclaimer, the term of this patent is extended or adjusted under 35 U.S.C. 154(b) by 0 days.

(21) Appl. No.: 16/753,512

(22) PCT Filed: Oct. 3, 2018

(86) PCT No.: PCT/IB2018/057690
§ 371 (c)(1),
(2) Date: Apr. 3, 2020

(87) PCT Pub. No.: WO2019/069253
PCT Pub. Date: Apr. 11, 2019

(65) Prior Publication Data
US 2020/0254048 A1    Aug. 13, 2020

(30) Foreign Application Priority Data

Oct. 4, 2017    (IT) .................... 102017000111261

(51) Int. Cl.
| | | |
|---|---|---|
| *A61K 36/537* | (2006.01) | |
| *A61K 9/00* | (2006.01) | |
| *A61K 31/12* | (2006.01) | |
| *A61K 31/201* | (2006.01) | |
| *A61K 31/385* | (2006.01) | |
| *A61K 36/30* | (2006.01) | |
| *A61P 25/02* | (2006.01) | |

(52) U.S. Cl.
CPC .......... *A61K 36/537* (2013.01); *A61K 9/0053* (2013.01); *A61K 9/0056* (2013.01); *A61K 31/12* (2013.01); *A61K 31/201* (2013.01); *A61K 31/385* (2013.01); *A61K 36/30* (2013.01); *A61P 25/02* (2018.01)

(58) Field of Classification Search
None
See application file for complete search history.

(56) References Cited

FOREIGN PATENT DOCUMENTS

| WO | WO 2016/027224 A1 | 2/2016 | |
|---|---|---|---|
| WO | WO-2016027224 A1 * | 2/2016 | ............. A61K 31/12 |
| WO | WO/2019/069253 A1 | 4/2019 | |

OTHER PUBLICATIONS

Horrobin et al. (1992) Agent and Action Suppl. vol. 37: 120-144. (Year: 1992).*
Guo et al. (2018) Molecular Neurodegeneration 13:4(13 pages). (Year: 2018).*
Parchikova et al. (2010) PLos One vol. 5, Issue 11 e14015 (8 pages). (Year: 2010).*
Yan et al. (2015) Chinese J. Nat. Med. 13(3): 163-182. (Year: 2015).*
Cotter et al. (1995) Diabetic neuropathy: new concepts and insights. vol. 1084; 257-262 (Year: 1995).*
Chun-Yan; S. et al., "Salvia miltiorrhiza: Traditional medicinal uses, chemistry, and Pharmacology," Chinese Journal of Natural Medicines 13(3): 163-82, Elsevier, Netherlands (2015).
Lin, T.Y. et al., "Tanshinone IIA, a constituent of Danshen, inhibits the release of glutamate in rat cerebrocortical nerve terminals," Journal of Ethnopharmacology 147(2): 488-96, Elsevier, Netherlands (2013).
Liu, Y et al., "Tanshinone IIA improves impaired nerve functions in experimental diabetic rats," Biochem Biophys Res Commun 399:49-54, Elsevier, Netherlands (2010).
Wang; B.Q., "Salvia miltiorrhiza: Chemical and pharmacological review of a medicinal plant," Journal of Medicinal Plants Research 4(25):2813-2820, Academic Journals, China (2010).
Xu, K. et al., "Effect of Tanshinone IIA in Preventing and Treating Oxaliplatin Induced Peripheral Neuropathy," Zhongguo Zhong Xi Yi Jie He Za Zhi(Chinese Journal of Integrated Traditional and Western Medicine) 36(5): 559-63, Zhongguo Zhong Xi Yi Jie He Za Zhi, China (2016).
International Search Report and Written Opinion for International Application No. PCT/IB2018/057690, European Patent Office, Germany, dated Jan. 22, 2019, 11 pages.
Bennett, G.J. and Xie, Y.K., "A peripheral mononeuropathy in rat that produces disorders of pain sensation like those seen in man," Pain 33(1):87-107, Elsevier, Netherlands (1988).
Cameron, N.E., et al., "Effects of alpha-lipoic acid on neurovascular function in diabetic rats: interaction with essential fatty acids," Diabetologia 41(4):390-399, Springer-Verlag, Germany (1998).
Colleoni, M. and Sacerdote, P., "Murine models of human neuropathic pain," Biochem. Biophys. Acta, 1802(10):924-933, Elsevier, Netherlands (2010).
Martucci, C., et al., "The purinergic antagonist PPADS reduces pain related behaviors and interleukin-1??, interleukin-6, iNOS and nNOS overproduction in central and peripheral nervous system after peripheral neuropathy in mice," Pain 137(1):81-95, Elsevier, Netherlands (2008).
Valsecchi, A.E., et al., "Genistein, a natural phytoestrogen from soy, relieves neuropathic pain following chronic constriction sciatic nerve injury in mice: Anti-inflammatory and antioxidant activity," J. Neurochem. 107(1):230-208, International Society for Neurochemistry, Canada (2008).
Zhu, C., et al., "Effects of Ginkgo Biloba Extract EGb-761 on Neuropathic Pain in Mice: Involvement of Opioid System," Phytother. Res, 30(11):1809-1816, Suppl. Figure, John Wiley & Sons, Ltd., United States (2016).

* cited by examiner

*Primary Examiner* — Russell G Fiebig
(74) *Attorney, Agent, or Firm* — Sterne, Kessler, Goldstein Fox P.L.L.C.

(57) ABSTRACT

The present invention relates to a composition comprising α-lipoic acid, *Salvia miltiorrhiza* extract and Curcumin, optionally further comprising γ-linolenic acid or borage oil. Furthermore, the present invention relates to the use of such composition for treating neuropathies.

7 Claims, No Drawings

COMPOSITION FOR THE TREATMENT OF METABOLIC AND MECHANICAL NEUROPATHIES

FIELD OF THE INVENTION

The present invention relates to a composition comprising α-lipoic acid, *Salvia miltiorrhiza* extract and Curcumin, optionally further comprising γ-linolenic acid or borage oil. Moreover, the present invention relates to the use of such composition for treating neuropathies. Such invention is based upon the synergic action of the above-mentioned active principles.

STATE OF ART

There are several types of polyneuropathies and several ways to classify them. In anatomo-pathological sense, for example, they can be classified in axonal if they affect the axon, or demyelinating if they affect Schwann cells. The best classification is the one based upon aetiology, which allows to classify neuropathies as follows:
1. Mechanical neuropathies
   a. Nervous compression syndrome
   b. Myelopathy
   c. Discopathy
   d. Lumboscatalgia
   e. Cervicobrachialgia
   f. Radiculopathy
2. Metabolic neuropathies
   a. Diabetic
   b. Uremic
   c. Hypothyroidism
3. Neuropathies from infectious agents
   a. HIV
   b. HCV
   c. Lepra
   d. Difteritis
   e. Eppstein-Barr virus
   f. Sarcoidosis
4. Toxic-food neuropathies
   a. Nutritional deficiency
   b. Alcoholic
   c. Environmental toxicity
   d. Drugs.
5. Demyelinating inflammatory polyneuropathies
6. Paraneoplastic polyneuropathies
7. Hereditary polyneuropathies.

As far as the neuropathy associated to diabetes is concerned, it is known that several forms thereof exist, theramong the main ones are the following:
   Sensorimotor polyneuropathy;
   Neuropathy of small fibres;
   Autonomic neuropathy,
   Neuropathic diabetic cachexia;
   Hypoglycaemic neuropathy;
   Neuropathy induced by pharmacological treatments;
   Polyradiculopathy;
   Diabetic radiculoplexopathy;
   Mononeuropathies;
   Cranial neuropathy.

The most frequent symptoms associated to diabetic neuropathy are: pain, cramps, paraesthesia and drowsiness. The pathogenesis mechanism of neuropathy in patients with diabetes mellitus is complex and not yet wholly explained. In the state of art several pharmacological treatments of neuropathy were proposed, such as for example analgesic drugs, antidepressants and anticonvulsants. However, these pharmacological treatments are characterized by reduced effectiveness, several side effects, moreover they not always act on the causes leading to the development of this pathology.

The object of the present invention is to provide a composition alternative to the ones known in the known state of art, useful in the treatment of neuropathic pain.

SUMMARY OF THE INVENTION

The present invention is based upon the search and identification of a new combination of active principles for the treatment of the neuropathic pain. Such compositions include or consist of a mixture of α-lipoic acid, *Salvia miltiorrhiza* extract and Curcumin, preferably such compositions further include γ-linolenic acid or borage oil. Other advantages and features of the present invention will result evident from the following detailed description.

DETAILED DESCRIPTION OF THE INVENTION

The present invention relates to a composition, in particular to a composition for oral use, comprising as main active ingredients: α-lipoic acid, *Salvia miltiorrhiza* extract and Curcumin and the use thereof for the treatment of neuropathic pain. The present invention allows to obtain contemporarily an antioxidant effect, an anti-inflammatory effect, a neuroprotective effect and an analgesic effect. Preferably the composition will include even γ-linolenic acid or borage oil in an amount between 1 mg and 500 mg.

The composition will include α-lipoic acid, preferably in an amount between 50 mg and 2000 mg. The composition could include *Salvia miltiorrhiza* extract titrated in an amount of tanshinoni between 1 mg and 500 mg.

The composition could further include an extract of *Curcuma longa* L. titrated in an amount of Curcumin between 1 mg and 1000 mg.

The composition could include γ-linolenic acid or an oil extracted from Borago officinalis, preferably in an amount between 1 mg and 500 mg.

The lipoic acid, even known as thioctic acid, or 1,2-thiolane-3-pentanoic acid is a carboxylic acid which can exist in an oxidized form and a reduced form (dihydrolipoic acid, DHLA). There are 2 enantiomers of this molecule: the biologically active form is the one with configuration (R), commonly called α-lipoic acid. In the animal and plant tissues there are small amounts of α-lipoic acid, mainly in form of lipoillysin, an amide formed by lipoic acid and lysin. The most abundant plant sources are spinach, broccoli and tomatoes which include 3.2, 0.9, and $0.6 \times 10^{-3}$ g of lipoillysin/g of dried product, respectively.

α-lipoic acid was identified in 1951 as cofactor of pyruvate decarboxylase enzyme and involved in the cycle of tricarboxylic acids (Krebs cycle).

α-lipoic acid enters the cell through several transportation systems, such as the transporter of medium chain fatty acids, a Na+ depending transportation system and, at intestinal level, a transporter of monocarboxylates correlated to protonic pump. Once in cytosol, this molecule is reduced to dihydrolipoic acid, through NAD(P)H-depending enzymes: mainly lipoamide dehydrogenase, but also thioredoxin reductase and glutathione reductase. The reduction mechanisms are highly tissue-specific.

This molecule is provided with a powerful antioxidant activity. It has both hydrophilic and hydrophobic properties, with LogP of 2.1: for this reason it can carry on its activity both at the level of cytosol and at the level of the cell membrane. A great number of studies shows that the reduced from of α-lipoic acid has a radical scavenger activity against reactive species of oxygen and nitrogen and it is capable of protecting the cells from damages of oxidative stress. Other studies show that the lipoic and dihydrolipoic acid are capable of reacting with hydroxyl radicals, with hypochlorous acid and singlet oxygen.

Heme oxygenase is a cytoprotective enzyme degrading heme. HO-1 isoform of this enzyme is inducible and up-regulated under conditions of oxidative stress and cell damage. It was shown that this protein is capable of inhibiting inflammation of microglia and astrocytes. The anti-inflammatory action also relates to the vascular cells, with inhibition of expression of adhesion molecules and pro-inflammatory cytokines. It was demonstrated that α-lipoic acid is capable of inducing the expression of HO-1 isoform of heme oxygenase by means of Nrf2 transcription factor.

α-lipoic acid increases the absorption of glucose by muscle tissues sensitive and resistant to insulin. The action mechanism consists in modulating the components of insulin signaling pathway. In particular, it was demonstrated that α-lipoic acid stimulates the re-distribution of the glucose transporters on the plasmatic membrane and the phosphorylation of IRS-1 (insulin receptor substrate 1). There is experimental evidence demonstrating the capability of α-lipoic acid of preventing the micro- and macrovascular complications in animal models of diabetes. Moreover, in a recent clinical study on patients affected by diabetes mellitus of type 1, the capability of α-lipoic acid was demonstrated of reducing the formation of AGE (final products of advanced glycosylation) and of reducing the activation of pathway of hexosamines, which contribute to many of the adverse effects of hyperglycaemia.

Thanks to the capability of α-lipoic acid of preventing the damages induced by hyperglycaemia, α-lipoic acid is capable of preventing the neuronal damage leading to diabetic neuropathy, apart from having the analgesic effect, which surely contribute to reduce the main symptom of this pathology. In fact, the selective inhibitory action of α-lipoic acid on the channels of calcium of type T was recently demonstrated: this contributes to the analgesic effect of this active principle by reducing the neuronal sensitivity to the neuropathic pain.

A great advantage of α-lipoic acid consists in the smaller incidence of side effects, with respect to the several pharmacological treatments currently used for the diabetic neuropathies.

α-lipoic acid could be present in the composition in an amount between 50 mg and 2000 mg.

*Salvia miltiorrhiza*, botanical name of the plant known as red salvia or Chinese salvia, is used very much in the traditional Chinese medicine for treating cerebrovascular and cardiovascular disorders, as well as the inflammatory pathologies. Tanshinoni, diterpene compounds with structure similar to that of abietane, are the main chemical compounds included inside *Salvia miltiorrhiza* extract. The main bioactive compounds are tanshinone I (TNI), tanshinone IIA (TNIIA) and cryptotanshinone (CPT). These compounds drew attention due to their different pharmacological effects, which include the anti-inflammatory and anti-tumour effect and the activities of cerebrovascular protection. Tanshinone IIA has potential effects against diabetes, neurodegenerative pathologies and cardiac hypertrophy. In addition to the anti-inflammatory and anti-tumour effects, tanshinone I has the capability of improving memory and learning ability and of improving memory disorders.

*Salvia miltiorrhiza* extract could be present in the composition in an amount between 50 mg and 2000 mg. *Curcuma longa* is a plant which has been used for thousands of years in the traditional Chinese medicine for the treatment of several types of pathologies. It is a perennial plant belonging to the family of Zingiberaceae and it is cultivated in India and in the Southeast Asian Nations. Curcuma longa mainly includes 3 secondary metabolites: curcumin (diferuloylmethane), demetoxycurcumin and bisdemetoxycurcumin.

Curcumin, the main secondary metabolite existing in the extract of Curcuma longa, is provided with several pharmacological activities, such as the anti-inflammatory, anti-oxidant, immunomodulatory, anti-tumour and neuro-protective activities. It is one of the most powerful anti-inflammatory drugs of natural origin.

Curcumin, preferably extracted from *Curcuma longa* L. could be present in the composition in an amount between 1 mg and 1000 mg. The composition of the invention could then include even an extract of plants belonging to the genus Curcuma, in particular belonging to the species *Curcuma longa*. For example, in the composition an extract of *Curcuma longa* can be present. Such extract will include the active principle curcumin titrated for example in the range comprised between 1% to 99% w/w.

In order to increase the bioavailability of the active ingredients, in particular of curcumin, the composition advantageously could include piperine, for example at least 20 mg. Piperine could be extracted from *Piper nigrum* or other plants of the genus Piper or of the family of Piperaceae. Still for increasing bioavailability of active ingredients, in particular of curcumin, the composition could further include nanoparticles, microparticles, liposomes or phospholipids used as carriers wherein one or more of the active ingredients of the composition are incapsulated. γ-linolenic acid ((6Z,9Z,12Z)-octadeca-6,9,12-trienoic acid) is an omega-6 fatty acid, which can be found mainly in the vegetable oils, in particular oil of *Borago officinalis* L.

If present, γ-linolenic acid, preferably extracted from *Borago officinalis* L., could be present in the composition in an amount between 1 mg and 500 mg. The composition of the invention then could include even an extract of plants belonging to the genus Borago, in particular belonging to the species *Borago officinalis, Borago longifolia, Borago morisiana, Borago trabutii*. For example an oil extracted from Borago officinalis could be present in the composition. Such raw material will include the active principle γ-linolenic acid titrated for example in the range comprised between 1% and 99% w/w.

The compositions according to the present invention can be formulated in any form and administration route and associated to any other component, in a variety of ways, preferably they will be formulated for oral use for example as capsules, soft capsules, tablets, pills, gelatins, powders or granules. Such excipients can be selected for example among those usually known in the state of art and include, but they are not limited thereto: a) carriers, such as for example sodium citrate and calcium phosphate, b) fillers such as for example starch, lactose, microcrystalline cellulose, sucrose, glucose, mannitol and colloidal silica, c) moistening agents, such as for example glycerol, d) disintegrants, such as alginates, calcium carbonate, starches, derivatives of starch, cellulose and polyvinylpyrrolidone, silicates and sodium carbonate e) binding agents such as carboxymethylcellulose, alginates, gelatin, polyvinylpyrrolidone, sucrose, polymeric derivatives of cellulose, derivatives of starch f) retarding agents such as paraffin, cellulose polymers, esters of fatty acids g) absorption accelerometers, such as quaternary ammonium compounds, h) soaking agents and surfactants such as cetyl alcohol and monostereate glycerol, i) adsorbents, such as benthic clays and kaolin, k) lubricants such as talcum, calcium stearate, magnesium stearate, polyethylene glycol, lauryl sulphate sodium, sodium stearylfumarate j) glidants such as talcum, colloidal silica.

The forms of solid dosage, such as tablets, capsules, soft capsules, gelatins, pills and granules, could be coated with enteric, gastric coatings or other types of coatings known in the state of art. They could include opacifier agents and they can be of the type so as to allow the release of the active ingredients only or preferably in a certain tract of the intestine, in case, in delayed way. Substances which can allow such delayed use include, but they are not limited thereto, polymers and waxes.

The soft capsules could house the antioxidant active substances in liquid form alone or in solutions, suspensions or emulsions of the active substances in a liquid solvent. The soft capsules could be characterized by a casing qualitatively similar to that of the stiff capsules but thicker and softer.

Liquid forms suitable to an oral administration for example are emulsions, solutions, prepared or extemporaneous suspensions, syrups and elixirs. Excipients suitable to the formulations according to the present invention in liquid forms for oral use include, but they are not limited thereto, diluents such as water or other solvents, solubilizing and emulsifying agents selected among ethyl alcohol, polyalcohols, propylene glycol, glycerol, polyethylenglycol and esters of sorbitan. These formulations can even include sweeteners and aroma. Particularly preferred formulations are conventional or delayed release tablets.

The compositions will be for example a medical device, food supplement, a nutraceutical, dietary and nutritional composition a foodstuff, a beverage, a nutraceutical, a medicament, a medicated food, a food for special medical purposes, a foodstuff or a cosmetic composition. The compositions will be mainly intended to be used by human beings, but they could also be used on animals.

The combination of the above-mentioned active ingredients could be used formulated in one single composition according to various above-described embodiments or in one kit including the different separated ingredients, for example in single compositions such as capsules, pills, tablets for sequential or contemporary administration of the different ingredients.

The above described compositions could be used/administered/ingested for the treatment of all types of neuropathies, in particular for one or more of the following neuropathies:

Mechanical Neuropathies
   a. Nervous compression syndrome
   b. Myelopathy
   c. Discopathy
   d. Lumboscatalgia
   e. Cervicobrachialgia
   f. Radiculopathy
2. Metabolic neuropathies
   a. Diabetic
   b. Uremic
   c. Hypothyroidism 3. Neuropathies from infectious agents
   a. HIV
   b. HCV
   c. Lepra
   d. Difteritis
   e. Eppstein-Barr virus
   f. Sarcoidosis
4. Toxic-food neuropathies
   a. Nutritional deficiency
   b. Alcoholic
   c. Environmental toxicity
   d. Drugs.
5. Demyelinating inflammatory polyneuropathies
6. Paraneoplastic polyneuropathies
7. Hereditary polyneuropathies.

As far as the neuropathy associated to diabetes is concerned, it is known that several forms exist thereamong there are the following ones:
   Sensorimotor polyneuropathy;
   Neuropathy of small fibres;
   Autonomic neuropathy,
   Neuropathic diabetic cachexia;
   Hypoglycaemic neuropathy;
   Neuropathy induced by pharmacological treatments;
   Polyradiculopathy;
   Diabetic radiculoplexopathy;
   Mononeuropathies;
   Cranial neuropathy.

EXAMPLES

Hereinafter some not limitative examples of daily dosages of the combination of the active ingredients used in the compositions of the present invention are shown.

Example 1

| Ingredient | Dose |
| --- | --- |
| α-lipoic acid | 400 mg |
| *Curcuma longa* L. rizoma, e.s. | 150 mg |
| *Salvia miltiorrhiza* Bge, radix e.s. | 150 mg |
| *Borago officinalis*, oleum | 100 mg |

Pharmaceutical form: prolonged release tablet.

Example 2

| Ingredient | Dose |
| --- | --- |
| α-lipoic acid | 400 mg |
| *Curcuma longa* L. rizoma, e.s. | 100 mg |
| *Salvia miltiorrhiza* Bge, radix e.s. | 75 mg |
| *Borago officinalis*, oleum | 50 mg |

Pharmaceutical form: prolonged release tablet.

Example 3

| Ingredient | Dose |
|---|---|
| α-lipoic acid | 600 mg |
| *Curcuma longa* L. rizoma, e.s. | 75 mg |
| *Salvia miltiorrhiza* Bge, radix e.s. | 50 mg |
| *Borago officinalis*, oleum | 25 mg |

Pharmaceutical form: prolonged release tablet.

Example 4

| Ingredient | Dose |
|---|---|
| α-lipoic acid | 800 mg |
| *Curcuma longa* L. rizoma, e.s. | 50 mg |
| *Salvia miltiorrhiza* Bge, radix e.s. | 25 mg |

Pharmaceutical form: prolonged release tablet.

Example 5

| Ingredient | Dose |
|---|---|
| α-lipoic acid | 800 mg |
| *Borago officinalis*, oleum | 50 mg |
| *Curcuma longa* L. rizoma, e.s. | 20 mg |
| *Salvia miltiorrhiza* Bge, radix e.s. | 10 mg |

Pharmaceutical form: prolonged release tablet.

Example 6

| Ingredient | Dosage (Conventional release layer) | Dosage (Prolonged release layer) |
|---|---|---|
| α-lipoic acid | 200 mg | 200 mg |
| *Curcuma longa* L. rizoma, e.s. | 75 mg | 75 mg |
| *Salvia miltiorrhiza* Bge, radix e.s. | 75 mg | 75 mg |
| *Borago officinalis*, oleum | 50 mg | 50 mg |

Pharmaceutical form: multi-layered tablet, with one conventional release layer and one modified release layer.

Example 7

| Active principle | Dosage (Conventional release layer) | Dosage (Prolonged release layer) |
|---|---|---|
| α-lipoic acid | 200 mg | 200 mg |
| *Curcuma longa* L. rizoma, e.s. | 100 mg | 100 mg |
| *Salvia miltiorrhiza* Bge, radix e.s. | 100 mg | 100 mg |
| *Borago officinalis*, oleum | 100 mg | 100 mg |

Pharmaceutical form: multi-layered layer, with one conventional release layer and one modified release layer.

Example 8

| Ingredient | Dose |
|---|---|
| α-lipoic acid | 600 mg |
| *Curcuma longa* L. rizoma, e.s. | 100 mg |
| *Salvia miltiorrhiza* Bge, radix e.s. | 100 mg |
| *Borago officinalis*, oleum | 100 mg |

Pharmaceutical form: prolonged release tablet.

Example 9

| Ingredient | Dose |
|---|---|
| α-lipoic acid | 600 mg |
| *Curcuma longa* L. rizoma, e.s. | 100 mg |
| *Salvia miltiorrhiza* Bge, radix e.s. | 50 mg |
| *Borago officinalis*, oleum | 50 mg |

Pharmaceutical form: prolonged release tablet.

Example 10

| Ingredient | Dose |
|---|---|
| α-lipoic acid | 900 mg |
| *Curcuma longa* L. rizoma, e.s. | 100 mg |
| *Salvia miltiorrhiza* Bge, radix e.s. | 50 mg |
| *Borago officinalis*, oleum | 50 mg |

Pharmaceutical form: prolonged release tablet.

Example 11

| Ingredient | Dose |
| --- | --- |
| α-lipoic acid | 900 mg |
| Curcuma longa L. rizoma, e.s. | 20 mg |
| Salvia miltiorrhiza Bge, radix e.s. | 10 mg |
| Borago officinalis, oleum | 10 mg |

Pharmaceutical form: prolonged release tablet.

Example 12

| Ingredient | Dose |
| --- | --- |
| α-lipoic acid | 600 mg |
| Curcuma longa L. rizoma, e.s. | 100 mg |
| Salvia miltiorrhiza Bge, radix e.s. | 50 mg |
| Borago officinalis, oleum | 50 mg |

Pharmaceutical form: conventional release tablet.

Example 13

| Ingredient | Dosage (Conventional release layer) | Dosage (Prolonged release layer) |
| --- | --- | --- |
| α-lipoic acid | 100 mg | 500 mg |
| Curcuma longa L. rizoma, e.s. | 33 mg | 167 mg |
| Salvia miltiorrhiza Bge, radix e.s. | 25 mg | 125 mg |
| Borago officinalis, oleum | 100 mg | — |

Pharmaceutical form: multi-layered layer, with one conventional release layer and one modified release layer.

Example 14

| Ingredient | Dose |
| --- | --- |
| α-lipoic acid | 800 mg |
| Curcuma longa L. rizoma, e.s. | 200 mg |
| Salvia miltiorrhiza Bge, radix e.s. | 100 mg |
| Borago officinalis, oleum | 50 mg |

Pharmaceutical form: Packet.

The compositions described in the examples were prepared according to the procedures known to the person skilled in the art, in particular by mixing ingredients in case with excipients and then reducing in form of tablet.

Experimental Data

Studies performed on the composition of the present invention for treating peripheral neuropathies.

Analgesic Action on Model of Mechanical Neuropathy

The sciatic nerve ligation (chronic constriction injury, CCI) is one of the most used models of neuropathic pain induced by mechanical damage, since it is reliable and easily reproducible [1]. It can be performed on rats [2], but even on mice [3]. For the study mice of type C57BL/6J were used. The animals, stabled in thermo-regulated room (temperature of 23 +/−2° C., humidity of 40-70%, cycles of light-dark of 12 hours), had free access to water and food (constituted by a standard diet). In order to perform the sciatic nerve ligation, the animals were anaesthetized by using a solution of pentobarbital sodium (at a dosage of 60 mg/kg) administered by intraperitoneal route. Afterwards, under a dissecting microscope, the sciatic nerve was exposed at half height of thigh and three ligations were performed near the nerve trifurcation, at a distance of 0.5 mm. The ligation was performed only on one of the mouse paws.

The formulations were administrated to mice by gavage tube for a period of 28 days.

The responses of mice to thermal hyperalgesia and to mechanical allodynia were recorded before administering the treatments and in the subsequent days.

Thermal hyperalgesia can be evaluated by means of a suitable apparatus, as previously described [4]. After having acclimated mice in cubicles made of plexiglas, a heat source was directed towards the plantar area of the rear paw of mice and the time in seconds was recorded elapsing from the activation of the heat source and the moment wherein the mouse moves the paw away from the latter.

The mechanical allodynia was quantified by stimulation with filaments of Von Frey, as described in literature [3], [5]. The animals were put in a small cage with a floor constituted by a metal grid. Subsequently a filament of von Frey was applied in the plantar area of the rear paw of the mouse, by exerting a growing force, until inducing the removal of the mouse paw from the filament. The mechanical pain tolerance level was measured separately on both paws, for four times. The final value, expressed in grams, derives from an average of the four measurements.

Anaelgesic Action on Model of Diabetic Neuropathy

In order to evaluate the analgesic effect of the composition on the diabetic neuropathy, diabetes was induced in mice, as previously shown in literature [6]. Briefly, the mice were treated with a high dosage of streptozocin, administered by intraperitoneal route, to induce diabetes. After 24 hours diabetes induction was confirmed by measuring glycaemia and glycosuria in not fasting mice.

After some weeks from diabetes induction, tests were performed to determine mechanical hyperalgesia and thermal allodynia, with the same experimental procedure used in mice with neuropathy due to sciatic nerve ligation.

Results

The data were analysed obtained by treating the above-described murine models with a composition comprising α-lipoic acid, Salvia miltiorrhiza extract and Curcumin and those obtained by treating the same murine models with a composition comprising only one of the three active principles with comparable dosage and administration mode. The comparison of the obtained data with the combination of the three active ingredients with respect to the treatment with anyone of the three ingredients designates a clear improvement in treating the pathology in the in-vivo model used for experimentation.

A More Detailed Description of the Experimental Drawing is Shown Hereinafter.

Objectives

1) Phenotypical characterization of animals subjected to peripheral neuropathy of 2 weeks with interest in the sensory component (tactile and thermal painful response).
2) Evaluation of the pharmacological effectiveness of the single compounds and of the related combinations in the behaviour alterations induced by neuropathy.
3) Study of the possible molecular and cell mechanisms underlying the potential neuroprotective effects of the above-mentioned compounds, by means of analysis of transcription factors and proteins in the different spinal and supraspinal areas involved in the mechanisms for inducing pain.

Treatment Scheme of Animal Groups
1. Sham (falsely operated)+Vehicle
2. SNI +Vehicle
3. SNI+α-lipoic acid (A) 20 mg/kg
4. SNI+*Curcuma longa* L. rizoma, e.s. (B) 10 mg/kg
5. SNI+*Salvia miltiorrhiza* Bge, radix e.s. (C) 10 mg/kg
6. SNI+A+B
7. SNI+A+C
8. SNI+B+C
9. SNI+A+B+C Induction of Neuropathy (SNI)

The neuropathy induced by means of the spared nerve injury (SNI) technique is performed by cutting the tibial and peroneal component of the sciatic nerve, by leaving intact the sural component. The animal is put under anaesthesia and after monitoring the depth of anaesthesia by checking the podal reflex, it is positioned in left side decubitus on a small bed, heated to keep constant the body temperature, one proceeds with trichotomy of the surgery field. The right rear limb is positioned on a small platform with the purpose of keeping it lifted and it is fastened with adhesive tape. On the area to be operated an incision is made in the side rear portion, above the thigh, by exposing the sciatic nerve. The latter originates from the spinal segments L4-L6 and divides into three branches, the sural nerve, the tibial nerve, the common peroneal nerve and this trifurcation is observed below the femoral biceps muscle. The common and tibial peroneal nerves are insulated from the sural nerve, bound with silk thread 5.0, and the cutting is performed at a distance between 2 and 4 mm from ligature; all this by avoiding stretching and the contact with the surgical tools of the sural nerve. The wound will be closed with one inner stitch and two outer stitches (absorbable surgical suture 6.0). The check animals (sham group) are subjected to the unique exposure of the nerve and subsequent closure of the cutaneous access.

Test for Evaluating Motor Deficits

In the Rotarod test (Ugo Basile, Varese, Italy) also called test of the rotating roller, the mouse is positioned on a rotating cylinder and the time is measured (in seconds) in which it is capable of remaining in equilibrium before falling. The cylinder is divided by 6 disks into 5 sections, by allowing to subject simultaneously 5 mice to the test, one per section. Therebelow there is a platform in turn divided into 5 dishes (at the 5 sections) each one thereof is connected to a magnet which, activated by the fall of the mouse on the dish, allows to record the residence time thereof on the cylinder. After an adaptation period of 30 seconds, the rotation speed is gradually increased from 3 to 30 rpm for a maximum time of 5 minutes. On the same day the animals are subjected to two tests separated therebetween by a time interval of one hour. The residence time of the mouse on the cylinder is expressed as latency (sec).

Test for Evaluating the Painful Behaviour

1) The tactile allodynia is measured by Von Frey. Such method provides the use of numbered filaments (Von Frey hairs) having different thickness, which give an incremental force according to a logarithmic scale. The animals are housed in cages made of plastics with a floor of metal grid. After a period of habituation of 30 minutes, the filaments are applied with constant force on the plantar surface of the rear paw for 3-5 seconds, with the purpose of determining the time of the response threshold. The mechanical threshold of withdrawing the paw is quantized by means of the up-down method which consists in applying as first filament the one corresponding to 50% of the threshold of withdrawing the paw under basal conditions and subsequently a filament of decreasing force or one of increasing force, in presence or absence of nociceptive response, respectively. Each measurement is performed at a distance of at least three minutes from the subsequent one, so as to avoid the presence of responses amplified due to close stimulations.

2) Hyperalgesia is evaluated by Plantar test (Ugo Basile, Varese, Italy). Each mouse is placed in a cage made of plexiglass (22 cm×17 cm×14 cm; length×length×height) with a bottom made of glass. After 1 hour of adaptation the plantar surface of the mouse paw is exposed to a beam of radiant heat through the bottom made of glass (Osram halogen bellaphot bulb; 8 V, 50 W). A photoelectric cell detects the light rejected by the paw and switches off the beam when the mouse, after the painful sensation, moves the paw by interrupting the beam of reflected light. The apparatus measures the time (in seconds) elapsing between the application of the stimulus and the nociceptive response of the animal. The maximum time of exposure to radiant heat is 10 seconds, so as to prevent possible tissue damages. The nociceptive response of the thermal sensitivity is expressed as latency of withdrawing the paw to the thermal stimulus (TWL, Thermal Withdrawal Latency). At the end of the behaviour tests all animals could be subjected to euthanasia and the organs thereof will be collected in order to process them for biochemical and immunohistochemical studies (Western blotting, PCR and Immunofluorescence). Such evaluations will be performed during the course of the pathological state and in presence of pharmacological treatment. In particular, the dosage of cytokines and pro/anti-inflammatory factors and the characterization of specific cell populations (neurons, glia, microglia) will be performed by means of the analysis of surface antigens and expression of receptors involved in the neuro-inflammatory processes associated to the onset and the development of the neuropathic pain.

BIBLIOGRAPHY OF EXPERIMENTAL PROTOCOLS

[1] M. Colleoni and P. Sacerdote, "Murine models of human neuropathic pain.," Biochim. Biophys. Acta, vol. 1802, no. 10, pp. 924-33, 2010.
[2] G. J. Bennett and Y. K. Xie, "A peripheral mononeuropathy in rat that produces disorders of pain sensation like those seen in man," Pain, vol. 33, no. 1, pp. 87-107, 1988.
[3] A. E. Valsecchi, S. Franchi, A. E. Panerai, P. Sacerdote, A. E. Trovato, and M. Colleoni, "Genistein, a natural phytoestrogen from soy, relieves neuropathic pain following chronic constriction sciatic nerve injury in mice:

Anti-inflammatory and antioxidant activity," J. Neurochem., vol. 107, no. 1, pp. 230-240, 2008.

[4] C. Martucci et al., "The purinergic antagonist PPADS reduces pain related behaviours and interleukin-1??, interleukin-6, iNOS and nNOS overproduction in central and peripheral nervous system after peripheral neuropathy in mice," Pain, vol. 137, no. 1, pp. 81-95, 2008.

[5] C. Zhu et al., "Effects of Ginkgo Biloba Extract EGb-761 on Neuropathic Pain in Mice: Involvement of Opioid System," Phyther. Res., vol. 30, nll, pp. 1809-1816, Nov. 2016.

[6] N. E. Cameron, M. A. Cotter, D. H. Horrobin, and H. J. Tritschler, "Effects of alpha-lipoic acid on neurovascular function in diabetic rats: interaction with essential fatty acids.," Diabetologia, vol. 41, no. 4, pp. 390-9, 1998.

The invention claimed is:

1. A method of treating neuropathies in a subject in need thereof comprising administering for a period of at least seven days a therapeutically equivalent amount of a composition comprising: (a) 75 mg α-lipoic acid, (b) 30mg *Salvia miltiorrhiza* extract, and (c) 20 mg Curcumin or an extract of plants belonging to the genus Curcuma that comprise curcumin, to the subject.

2. The method of claim 1 wherein said neuropathies are mechanical neuropathies, metabolic neuropathies, neuropathies from infectious agents, demyelinating inflammatory polyneuropathies, paraneoplastic polyneuropathies, hereditary polyneuropathies, and/or neuropathies induced by pharmacological treatments.

3. The method of claim 2 wherein said neuropathies are mechanical neuropathies associated with Nervous compression syndrome, Myelopathy, Discopathy, Lumboscatalgia, Cervicobrachialgia, radiculopathy or metabolic neuropathies associated with Diabetes, Uraemia or Hypothyroidism or Neuropathy associated with infectious agents selected from HIV, HCV, Lepra, Difteritis, Epstein-Barr virus, Sarcoidosis or Toxic-food neuropathies due to a nutritional deficiency, alcohol or environmental toxicity.

4. The method of claim 1, wherein the composition further comprises γ-linolenic acid or borage oil.

5. The method of claim 1, wherein the composition further comprises piperine or an extract of plants belonging to the Piperaceae family comprising piperine.

6. The method of claim 1, wherein the composition is administered in the form of a capsule, soft capsule, tablet, pill, gelatin, powder, granule, emulsion, solution, syrup, or prolonged release tablet.

7. The method of claim 1, wherein the composition is a medical device, a food supplement, a nutraceutical, dietary and nutritional composition, a foodstuff, a beverage, a nutraceutical, a medicament, a medicated food, a food for special medical purposes or a cosmetic composition.

* * * * *